United States Patent
Aoki et al.

(10) Patent No.: US 8,663,577 B2
(45) Date of Patent: Mar. 4, 2014

(54) VARIABLE PITCH ARRAY SPOTTER

(75) Inventors: Hiroshi Aoki, Tsukuba (JP); Masaki Torimura, Tsukuba (JP); Hiroaki Tao, Tsukuba (JP); Takashi Ikeda, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 647 days.

(21) Appl. No.: 12/385,755

(22) Filed: Apr. 17, 2009

(65) Prior Publication Data

US 2009/0233816 A1    Sep. 17, 2009

Related U.S. Application Data

(63) Continuation-in-part of application No. 12/309,072, filed as application No. PCT/JP2007/062926 on Jun. 27, 2007, now abandoned.

(30) Foreign Application Priority Data

Jul. 12, 2006 (JP) .................. 2006-192000
Mar. 12, 2007 (JP) .................. 2007-061165

(51) Int. Cl.
*B01L 3/00* (2006.01)
(52) U.S. Cl.
USPC ........... 422/501; 422/504; 422/521; 422/564; 422/566; 422/519; 436/180; 73/863.32
(58) Field of Classification Search
USPC ......... 422/100, 501, 504, 520, 521, 515, 524, 422/519, 564, 566; 73/864.11, 864.31, 73/863.32, 863.31; 436/180
See application file for complete search history.

(56) References Cited

U.S. PATENT DOCUMENTS

| | | | | |
|---|---|---|---|---|
| 3,834,876 | A * | 9/1974 | Kormendy et al. | 422/566 |
| 4,116,638 | A * | 9/1978 | Kenoff | 422/562 |
| 5,061,449 | A | 10/1991 | Torti et al. | |
| 5,312,757 | A * | 5/1994 | Matsuyama et al. | 436/54 |
| 5,335,481 | A * | 8/1994 | Ward | 53/446 |
| 6,235,244 | B1 * | 5/2001 | Allen et al. | 422/525 |
| 6,451,263 | B1 | 9/2002 | Sarrine | |
| 6,592,819 | B1 * | 7/2003 | Ogura | 422/63 |
| 2003/0223910 | A1 * | 12/2003 | Jackson et al. | 422/100 |

FOREIGN PATENT DOCUMENTS

| | | |
|---|---|---|
| JP | A-55-4523 | 1/1980 |
| JP | A-62-1459 | 1/1987 |
| JP | A-9-318636 | 12/1997 |
| JP | A-10-48100 | 2/1998 |

(Continued)

OTHER PUBLICATIONS

Apr. 30, 2013 Official Notice of Rejection issued in Japanese Patent Application No. 2010-267350 (with English translation).

*Primary Examiner* — Lyle Alexander
(74) *Attorney, Agent, or Firm* — Oliff & Berridge, PLC

(57) ABSTRACT

A spotter that includes a plurality of spotting heads, each of the plurality of spotting heads having a discharging portion at a tip portion, the plurality of spotting heads form an m×n array (m, n>1) with m spotting heads arranged lengthwise and n spotting heads arranged crosswise; and a pitch varying mechanism configured to vary an array pitch of the plurality of spotting heads arrayed in a lengthwise direction and an array pitch of the plurality of spotting heads arrayed in a crosswise direction.

7 Claims, 22 Drawing Sheets

(56) References Cited

FOREIGN PATENT DOCUMENTS

| | | |
|---|---|---|
| JP | A-10-503841 | 4/1998 |
| JP | A-10-293089 | 11/1998 |
| JP | A-2001-99847 | 4/2001 |
| JP | A-2001-179113 | 7/2001 |
| JP | A-2001-211873 | 8/2001 |
| JP | A-2003-315352 | 11/2003 |
| JP | A-2005-91339 | 4/2005 |
| WO | WO 95/35505 | 12/1995 |
| WO | WO 00/47249 | 8/2000 |

* cited by examiner

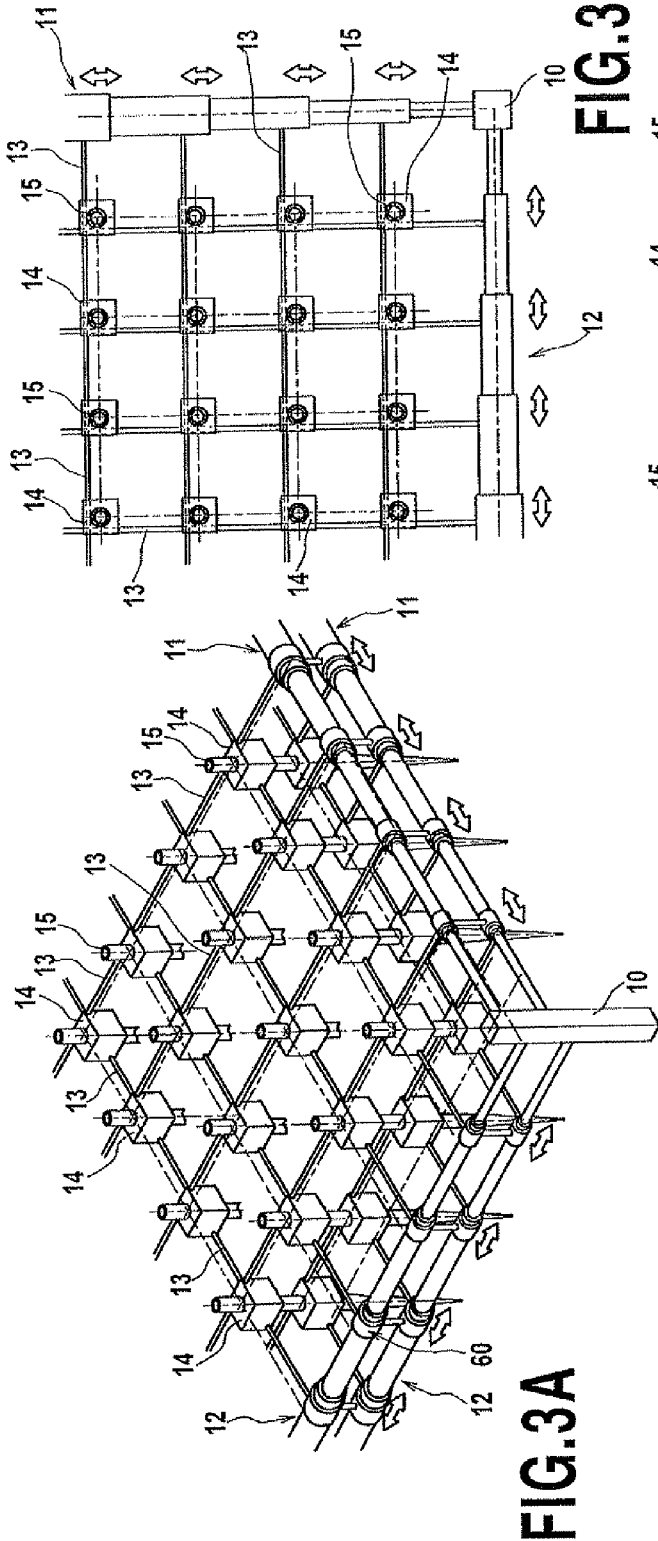
FIG.3A
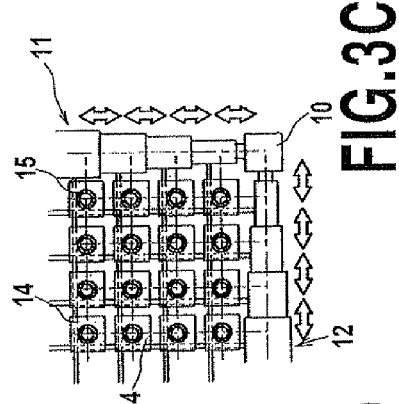
FIG.3B
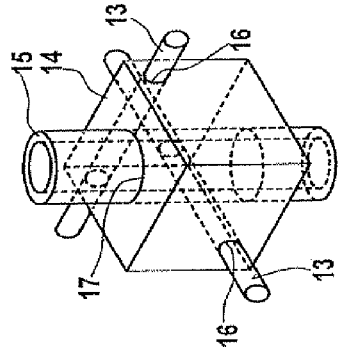
FIG.3C
FIG.3D
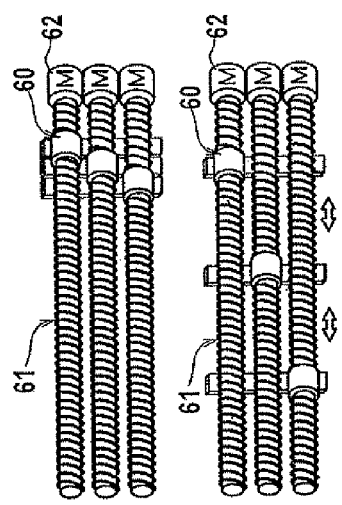
FIG.3E
FIG.3F

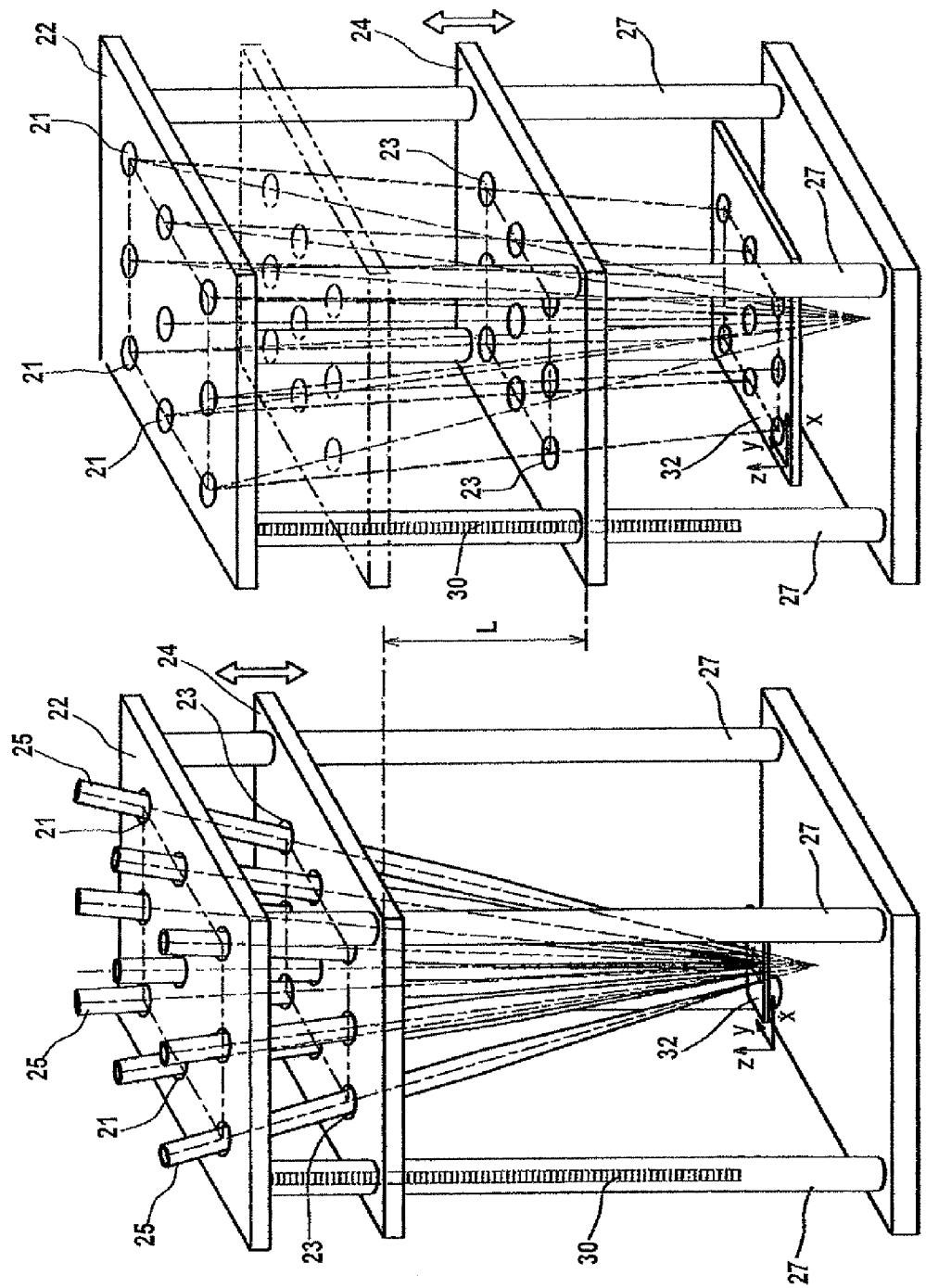

TYPES OF CHANGES IN ARRAY SHAPE OF ARRAY SPOTS

CONGRUENT CHANGE TYPE

SIMILAR CHANGE TYPE

AFFINE CHANGE TYPE

PROJECTIVE CHANGE TYPE

OTHERS
PHASE CHANGE TYPE
(A FLAT-PLANE ARRAY CHANGED TO A CURVED-SURFACE ARRAY) ETC

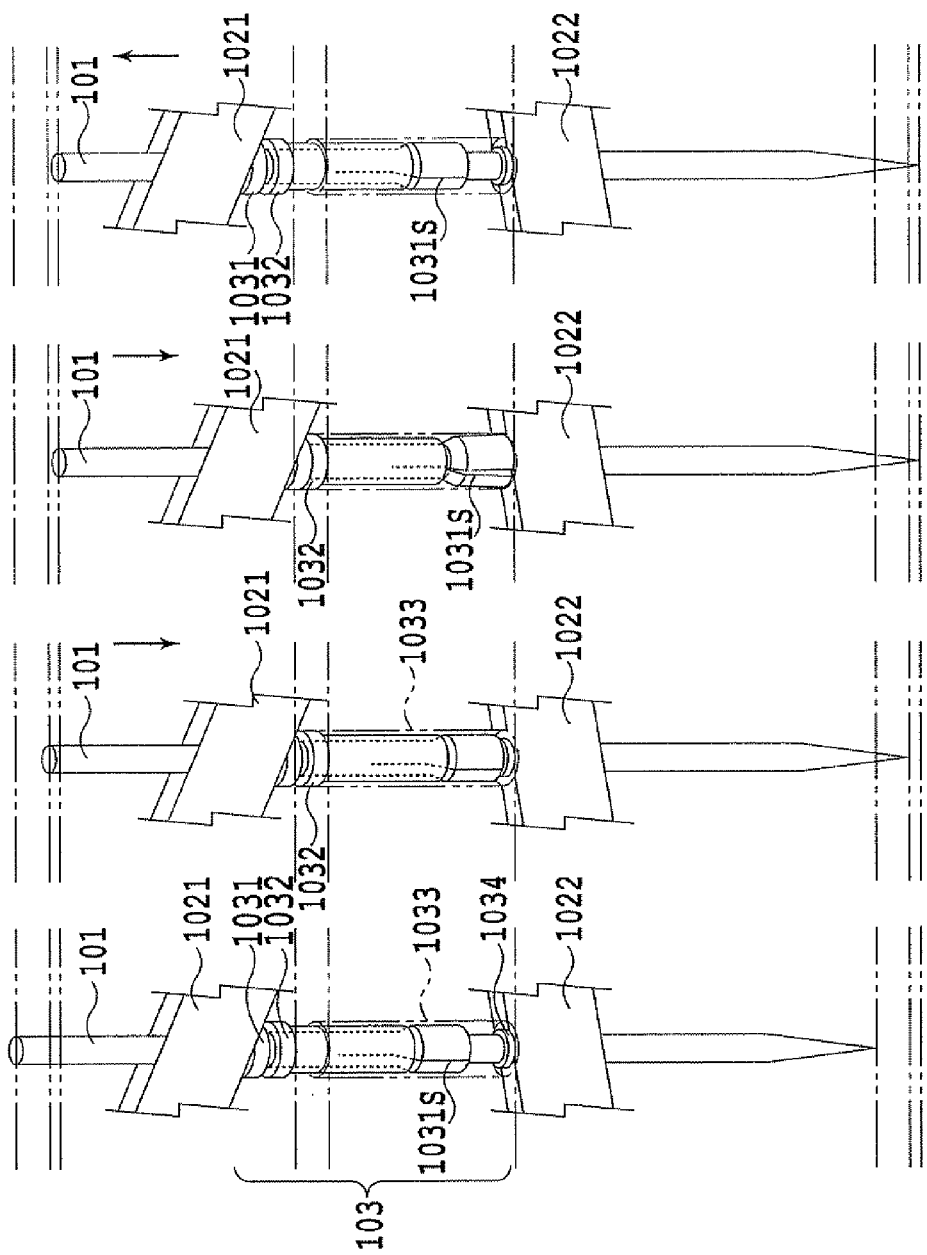

VARIABLE PITCH ARRAY SPOTTER

CROSS-REFERENCE TO RELATED APPLICATIONS AND INCORPORATION BY REFERENCE

This application is a continuation-in-part Application of U.S. patent application Ser. No. 12/309,072 filed on Jan. 6, 2009. The full disclosures of all of the above-listed patent applications are hereby incorporated by reference.

BACKGROUND OF THE INVENTION

1. Field of the Invention The present invention relates to a spotter equipped with plural variable-pitch spotting heads to spot simultaneously, onto plural spotting positions arranged in an array, sample solutions collected from plural sample containers, respectively.

2. Description of the Related Art

In the development of array chips on which plural kinds of DNAs or proteins are placed, the sample solutions need to be spotted in an array within an area of several centimeters square on a substrate, such as a glass slide. Various automated spotter have been developed thus far for the purpose of carrying out the spotting to this end. Such an automated spotter includes, as its spotting heads, plural spotting heads including discharging portions, such as pins and pipette tips, and automatically carries out the following processes: collecting sample solutions from sample containers; then, spotting the solutions onto predetermined positions on a substrate; and, after that, washing the discharging portions, or disposing the discharging portions to replace them with unused discharging portions. Microtiter plates with 96 wells, 384 wells and 1536 wells are frequently-used examples of the sample containers. The wells of these Microtiter plates are arranged with arrays of 9 mm, 4.5 mm and 2.25 mm, respectively. On the other hand, when the spotting onto a substrate is carried out, the solutions are spotted at intervals ranging from several tens of micrometers to several hundreds of micrometers. Accordingly, in the spotting from sample containers, such as a Microtiter plate, onto a substrate, the array pitch of the spotting heads has to be changed in one way or another.

Conventional automated spotters are roughly classified into the following two groups. Each spotter of a first group includes plural variable-array spotting heads that are arranged along a straight line. Each spotter of the second group includes plural invariable-array spotting heads that are arranged in an array. The spotters of the first group employ pipette tips or needles as the discharging portions of their spotting heads. The minimum value of the array pitch of the spotting heads is restricted by the outer dimensions of each spotting head. Accordingly, the pitch varying mechanism is used only when the collecting and spotting of the sample solutions is performed between arrays of sample containers, such as Microtiter plates, having different array from each other (see Patent Documents 1, 2, 3 and 4). In spotting with a pitch smaller than the above case, each of the spotters carries out the spotting while shifting the spotting heads.

In spotting the sample solutions directly onto a substrate, the spotter spots one kind of sample solution by using one of the spotting heads at a time, and thus cannot achieve its full potential. The spotters of the second group employ pins as the discharging portions of their spotting heads, and the array of the spotting heads is not variable. Accordingly, the spotting heads of the spotter are formed with the same array as the Microtiter plate. The spotter carries out the spotting of the collected sample solutions to the due spotting positions simply by shifting the pitch (see Patent Documents 5 and 6).

As described above, conventional automated spotters are not designed for the purpose of spotting, directly onto a substrate, sample solutions collected from sample containers, and thus have the following problem. It takes a lot of time for such conventional automated spotters to carry out the spotting onto a single substrate. In addition, the more the total number of necessary spots becomes, the longer it takes for these spotters to finish spotting onto all the positions that need spotting. This problem, however, seems to be solved somewhat when the spotting is simultaneously carried out onto plural substrates so as to prepare plural substrates with identical spotting arrays, since time taken to spot samples on one substrate is relatively reduced. In contrast, for example, in the case of a small lot preparation of substrates, or in a case where the spotting array pitch needs to be changed frequently, the conventional automated spotters have no advantages. Accordingly, it is evident that the above-mentioned problem is left unsolved in its fundamental sense.

Patent Document 1: Japanese Patent Laid-Open No. HO 9-318636 (1997)

Patent Document 2: Japanese Patent Laid-Open. No. H10-48100 (1998)

Patent Document 3: Japanese Patent Laid-Open No. 2003-315352

Patent Document 4: Japanese Patent Laid-Open No. 2005-91339

Patent Document 5: WO 95/35505

Patent Document 6: Japanese Patent Laid-Open No. H10-503841 (1998)

SUMMARY OF THE INVENTION

Accordingly, the present invention aims to provide an automated spotter capable of efficiently carrying out the simultaneous spotting of plural kinds of solutions onto a substrate in an array.

MEANS FOR SOLVING THE PROBLEMS

An automated spotter according to the present invention is equipped with a mechanism which includes plural spotting heads arranged in an array shape and which is capable of spotting simultaneously plural kinds of sample solutions directly onto a substrate. Specifically, the automated spotter of the present invention is characterized by including a mechanism to vary the pitch between each of the spotting heads so as to correspond to two different states of the pitch—a pitch at the time of collecting the solutions and another pitch at the time of spotting the solutions. The mechanism makes it possible to carry out the simultaneous spotting of plural kinds of sample solutions directly onto a substrate. Accordingly, even when the total number of spots to be formed is increased, the work of preparing the substrate can be finished with a single round of collection-and-spotting operations by increasing the number of spots that are simultaneously formed by means of an increased number of spotting heads. As to conventional automated spotters, as the number of handlings is increased and the amount of the solutions to be included in each spot is decreased along with the increase in the total number of spots to be formed, the repeatability for every spotting and the overall reliability are impaired. The automated spotter of the present invention can enhance the repeatability and the reliability by carrying out the spotting simultaneously, at one time, and in an array shape. In addition, the automated spotter of the present invention employs fine-bore tubes as its spotting heads for the purpose of dealing with a case of the spotting pitch ranging from several tens of micrometers to several hundreds of micrometers.

An invention according to claim 1 provides a spotter with the following configuration. The spotter includes a plurality of spotting heads each of which includes a discharging portion at a tip portion. The plurality of spotting heads form an m×n array (m, n≥1) with m spotting heads arranged lengthwise and n spotting heads arranged crosswise. In addition, the spotter includes a mechanism capable of changing an array pitch of the plurality of spotting heads in lengthwise and crosswise directions. With this configuration, the plurality of spotting heads form an array, and the direct spotting from the sample containers onto the substrate is made possible by changing the array pitch between the time of the collection and the time of the spotting.

Another invention provides the spotter according to claim 1 with the following configurations. Not only the discharging portions but also the entire bodies of the spotting heads are made of fine-bore tubes, such as capillaries, needles, and glass tubes. Accordingly, the spotter is equipped with a mechanism capable of narrowing the array pitch of the plurality of the spotting heads down to a length corresponding to outer dimensions of the fine-bore tube. With this mechanism, the spotter can carry out the spotting at intervals each of which ranges from several tens of micrometers to several hundreds of micrometers.

In another invention, the mechanism capable of changing the array pitch of the plurality of spotting heads in the lengthwise and crosswise direction holds the plurality of spotting heads by means of supporting tools fixed to the respective spotting heads and supporting tools slidably reciprocable on the spotting head. In addition, the mechanism forms pantographs by rotatably connecting unit links each including a pair of shafts rotatably coupled to each other at their middle points so as to form an X shape, the shafts being connected to the two kinds of supporting tools at their end portions so as to alternate in each of their lengthwise and crosswise directions. The mechanism may preferably adjust the array pitch of the plurality of the spotting heads so as to be identical to the array pitch of a plurality of sample containers arranged in at an even pitch, and so as to be identical to the array of the positions where sample solutions are to be spotted. The mechanism may preferably make the plurality of spotting heads carry out the simultaneous spotting of a plurality of sample solutions in an array shape. The mechanism may preferably include a mechanism that allows the plurality of spotting heads to keep distances between adjacent spotting heads equal to one another when the pitch is wide, allows adjacent ones of the plurality of spotting heads to be in contact with one another when the pitch is narrow, and is capable of maintaining the discharging portions of the plurality of spotting heads on a single plane both when the pitch is wide and when the pitch is narrow.

Another invention has the following configuration. The mechanism capable of changing the array pitch of the plurality of spotting heads in the lengthwise and crosswise direction includes two stretchable shafts provided with bar-shape guide rods extending perpendicularly to the shafts. The mechanism includes support tools provided at lattice points of a lattice formed with the two shaft and the guide rods by making the two shafts orthogonal to each other. The support tools support the plurality of spotting heads laid out in the up-and-down direction. The mechanism includes a mechanism that slidably reciprocates the plurality of spotting heads on the guide rods by means of the support tools. The mechanism may preferably adjust the array pitch of the plurality of the spotting heads so as to be identical to the array pitch of a plurality of sample containers arranged in at an even pitch, and so as to be identical to the array of the positions where sample solutions are to be spotted. The mechanism may preferably make the plurality of spotting heads carry out the simultaneous spotting of a plurality of sample solutions in an array shape. The mechanism may preferably include a mechanism that allows the plurality of spotting heads to keep distances between adjacent spotting heads equal to one another when the pitch is wide, allows adjacent ones of the plurality of spotting heads to be in contact with one another when the pitch is narrow, and is capable of maintaining the discharging portions of the plurality of spotting heads on a single plane both when the pitch is wide and when the pitch is narrow.

Another invention has the following configuration. The mechanism capable of changing the array pitch of the plurality of spotting heads in the lengthwise and crosswise directions includes a mechanism that keeps a plate having holes formed in an array corresponding to spotting positions and a plate having holes formed in an array that is similar to the hole array corresponding to the spotting positions so as to make the plates vertically parallel to each other with a distance left in between. The mechanism slidably holds the plurality of spotting heads by allowing each spotting head to penetrate two holes of the respective plates, the two holes being located at a position of similarity. The mechanism makes the array pitch of the plurality of spotting heads larger or smaller by widening or narrowing the distance between the two plates. Stoppers are provided to the plurality of the spotting heads so as to make the discharging portions of the plurality of spotting heads form a single flat plane when the array pitch is controlled. The mechanism may preferably adjust the array pitch of the plurality of the spotting heads so as to be identical to the array pitch of a plurality of sample containers arranged in at an even pitch, and so as to be identical to the array of the positions where sample solutions are to be spotted. The mechanism may preferably make the plurality of spotting heads carry out the simultaneous spotting of a plurality of sample solutions in an array shape. The mechanism may preferably include a mechanism that allows the plurality of spotting heads to keep distances between adjacent spotting heads equal to one another when the pitch is wide, allows adjacent ones of the plurality of spotting heads to be in contact with one another when the pitch is narrow, and is capable of maintaining the discharging portions of the plurality of spotting heads on a single plane both when the pitch is wide and when the pitch is narrow.

Another invention has the following configuration. The mechanism capable of changing the array of the plurality of spotting heads in the lengthwise and crosswise directions includes a mechanism that keeps two plates each having a plurality of (open) grooves whose first ends are arranged with a pitch corresponding to a state before the spotting and whose second ends are arranged with a pitch corresponding to a state after the spotting so as to make the plates vertically parallel to each other with a distance left in between and to make the grooves in one of the two plates be horizontally orthogonal to the grooves in the other plate, slidably holds the plurality of spotting heads by allowing each spotting head to penetrate a lattice point of a lattice formed with the two grooves of the respective plates, and makes the array pitch of the plurality of spotting heads larger or smaller by reciprocally moving the two plates. The mechanism may preferably adjust the pitch of the plurality of the spotting heads so as to be identical to the array of a plurality of sample containers arranged in at an even pitch, and so as to be identical to the array of the positions where sample solutions are to be spotted. The mechanism may preferably make the plurality of spotting heads carry out the simultaneous spotting of a plurality of sample solutions in an array shape. The mechanism may preferably include a mechanism that allows the plurality of spotting heads to keep distances between adjacent spotting heads equal to one another when the pitch is wide, allows adjacent ones of the plurality of spotting heads to be in contact with one another when the pitch is narrow, and is capable of maintaining the discharging portions of the plurality of spotting heads on a single plane both when the pitch is wide and when the pitch is narrow.

The spotter according to another aspect of the present invention has a plurality of capillaries with flexibility, and a pitch varying mechanism configured to movably guide the capillaries in a predetermined direction so as to arrange the plurality of the capillaries in a form of an array and to vary an array pitch of the plurality of capillaries in lengthwise and crosswise directions.

With the above-described configurations, the present invention is capable of performing the simultaneous spotting of plural kinds of solutions onto a substrate. Accordingly, even when the total number of spots to be formed is increased, the spotting work can be finished in a shorter length of time by increasing the number of spots to be formed simultaneously, which is made possible by employing a larger number of spotting heads. Thus, all the solutions on one Microtiter plate can be spotted on to a substrate with a single spotting operation, so that a DNA microarray or like used in generic testing or the like and a target plate used in mass analyzers or the like can be prepared quickly and easily. As a consequence, a significant improvement in efficiency can be expected for the multiple-sample simultaneous detection based on the above-mentioned techniques. As to conventional automated spotters, as the number of handlings is increased and the amount of the solutions to be included in each spot is decreased along with the increase in the total number of spots to be formed, the repeatability for every spotting and the overall reliability are impaired. The repeatability and the reliability can be enhanced by the simultaneous spotting in an array shape carried out in a single spotting operation. In addition, the present invention has a significant advantage when the spotting has to be finished in a short length of time, for example, when biomaterials that tend to be degraded easily, such as proteins and nucleic acids, or living matters, such as cells and coli bacteria are involved in the detection.

Further features of the present invention will become apparent from the following description of exemplary embodiments (with reference to the attached drawings).

BRIEF DESCRIPTION OF THE DRAWINGS

FIGS. 3A to 3F are views illustrating an example of a stretchable-rod-type spotting-head-pitch varying apparatus according to a second embodiment of the present invention;

FIGS. 4A and 4B are views illustrating an example of a perforated-plate-type spotting-head-pitch varying apparatus according to a third embodiment of the present invention;

FIGS. 18A to 18D are views illustrating operations of a clamping mechanism in the pitch varying mechanism in FIGS. 12A and 12B;

DESCRIPTION OF THE EMBODIMENTS

The present invention aims to provide an automated spotter capable of more efficiently performing the simultaneous spotting of plural kinds of solutions onto a substrate in an array shape. The present invention accomplishes this object by providing a spotter including plural spotting heads with discharging portions at their respective tip portions, the plural spotting heads forming an m×n array (m, n≥1) with m spotting heads arranged lengthwise and n spotting heads crosswise, and the provided spotter is equipped with a mechanism that can change both the pitch with which the spotting heads are arrayed lengthwise and the pitch with which the spotting heads are arrayed crosswise.

FIGS. 1 to 23 illustrate the configurations of pitch varying mechanisms for spotters according to various embodiments of the present invention. These embodiments describe automated spotters each of which is built in an array-chip preparing apparatus commonly used, for example, in medical testing, and each of which collects plural samples from sample containers, such as Microtiter plate, at a time and spots the collected samples onto a substrate at a time in the array-chip preparing apparatus. Note that these drawings are illustrated schematically without details for the sake of easier understanding of the content of the present invention.

First Embodiment

Figure 1A:
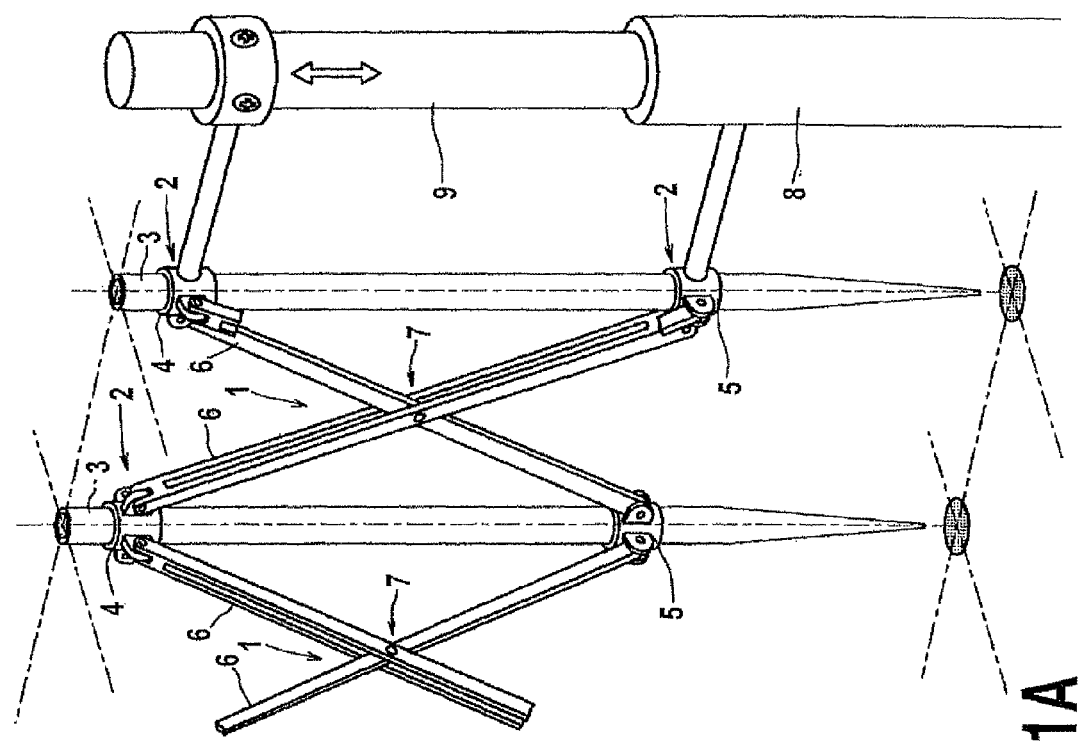
FIGS. 1A to 1C are views illustrating an example of a pantograph-type spotting-head-pitch varying apparatus according to a first embodiment of the present invention.
Figure 1B:
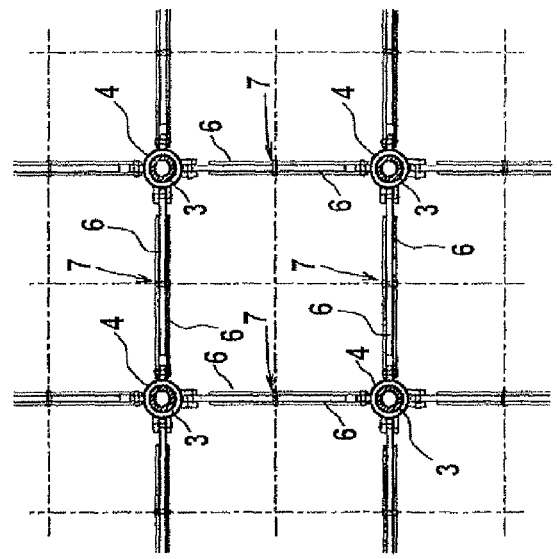
Figure 1C:
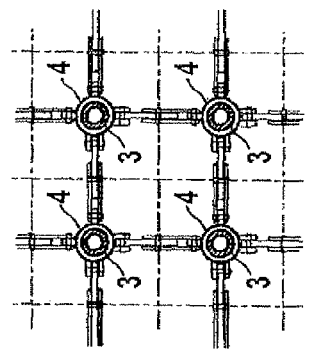

FIGS. 1A to 1C show an example of the use of a mechanism where, at each lattice point 2 of pantographs 1 as unit links constituting a pantograph lattice formed in a lattice shape, a capillary 3 is held perpendicularly to the pantograph lattice, and where the distance between each two adjacent capillaries 3 widens or narrows as the pantograph lattice widens or narrows. The pantograph 1 includes: rings 4 and 5 as support tools to be lattice points; and shafts 6 linking the rings with one another. Each of the capillaries 3 is supported by the two rings 4 and 5 attached respectively to the upper and lower ends of two intersecting shafts. The two shafts are fixed to each other at an intersection 7 so as to be free to rotate. In the illustrated embodiment, the lower ring 5 is a fixed ring fixed to the main body of the capillary 3, but the upper ring 4 is a movable ring that moves freely up and down in the axial direction of the capillary 3 in conjunction with the stretching or contracting of the pantograph 1. The stretching or the contracting of the lattice distance can be accomplished by an up-and-down reciprocating motion of the movable ring at an arbitrarily-chosen lattice point in a pantograph 1. In the illustrated embodiment, example is shown where one of the upper rings 4 is fixed to a movable rod 9 designed to be moved, inside a fixed rod 8, up and down by an unillustrated motor or the like.

Figure 2A:
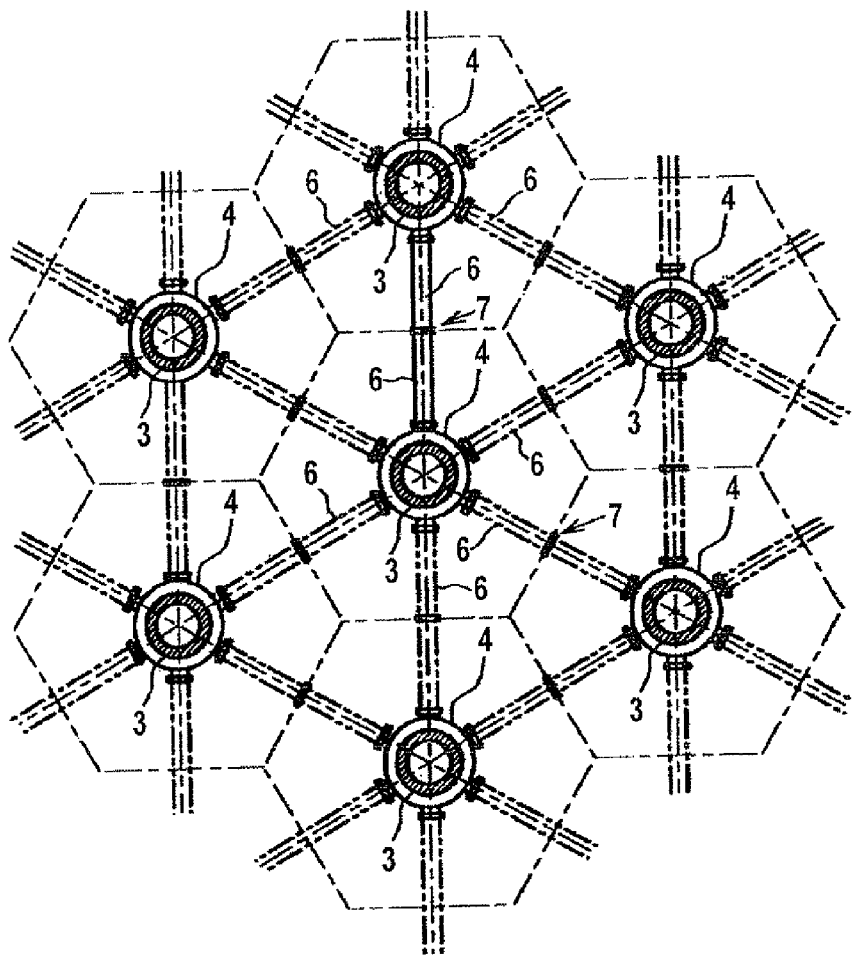
FIGS. 2A and 2B are views illustrating another form of the first embodiment.
Figure 2B:
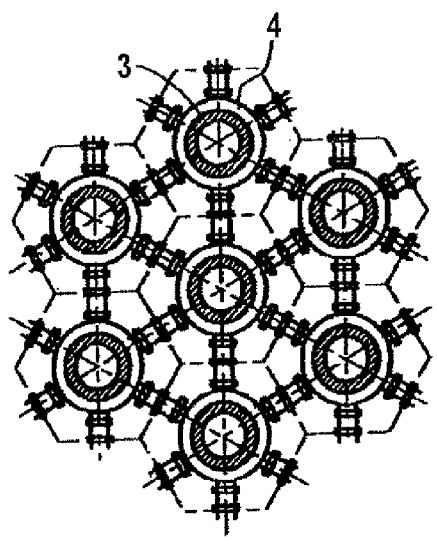

The use of such a mechanism of the pantographs 1 allows all the capillaries to move in parallel to one another, so that the ends of all the capillaries can always stay within a single plane. This pantograph lattice is formed in a parallelogram shape as shown in FIGS. 1B and 1C, or in a parallel-hexagonal shape as shown in FIGS. 2A and 2B. Preferably, the pantograph lattice is formed in a shape of a square or of a regular hexagon as illustrated. In the pantograph lattice of regular hexagon illustrated in FIG. 2A to 2C, the capillaries are collected or distributed in a close-packed fashion. The pitch of the plural spotting heads is adjusted by such mechanism so as to be identical to the evenly-arranged array of the plural sample containers, and to be identical to the array of the spotting position for the sample solutions.

Second Embodiment

In the embodiment illustrated in FIG. 3A to 3E, two shafts are orthogonalized to a support column 10, and two sets of the two shafts are provided to support capillaries at the lower and upper levels. Here, each shaft is made stretchable by installing each stage of the shaft inside the subsequent stage thereof. Guide-rod holders 60 are provided to all the stages of shafts 11 and 12. Guide rods 13 made of slim bars are made to extend in parallel to one another respectively from the guide-rod holders 60 to unillustrated opposite shafts. Holders 14 are provided respectively at lattice positions of a lattice thus formed by the shafts 11, 12 and guide rods 13, and capillaries 15 are held respectively by the holders 14. As FIGS. 3B and 3C illustrate, in the mechanism thus formed, the stretching or the contracting of the stretchable shafts 11 and 12 expands or diminishes the size of the lattice so as to widen or narrow each inter-capillary distance. As FIG. 3D illustrates, in each holder 14 holding the capillary 15, through-holes 16 are formed to allow the holder 14 to move freely on the guide rods 13 and a perpendicular-hole 17 is formed to hold the capillary. These holes formed in each holder 14 are preferably offset from one another vertically and horizontally so as not to intersect one another. As FIGS. 3E and 3F illustrate, the mechanism to widen or narrow the pitch may employ, instead of the stretchable shafts, a combination of threaded shafts 61 provided respectively with motors 62 and guide-rod holders 60 that are female-threaded so as to mesh with the threaded surface of the threaded shafts 61. Alternatively, pantographs described in Embodiment 1 may be employed to this end. Some of the capillaries may be provided to the guide-rod holders 60 and not to the holders 14. In addition, stages of each shaft are preferably equidistant.

Third Embodiment

A mechanism employed in the embodiment illustrated in FIGS. 4A and 4B has the following configuration. An upper plate 22 with holes 21 formed equidistantly and a lower plate 24 with holes 23 formed at intervals widened, from the intervals of the holes 21, both lengthwise and crosswise by equal factors are provided in parallel to each other with the lower plate 24 placed below the upper plate 22. Each capillary 25 is inserted through one of the holes in the plate 22 and through one of the holes in the plate 23 (24) that is located at the symmetrical position to the above-mentioned hole. The upwards or downwards movement of the lower plate 24 widens or narrows the distance between the ends of each adjacent capillaries 25 that stick out downwards from the lower plate 24. In the illustrated embodiment, the holes 21 formed in the upper plate 22 held by support columns 27 hold the capillaries 25 with a force that is made sufficiently strong by use of elastic bodies or the like in the holes 21, while allowing the capillaries 25 to move swinging in the corresponding holes 23.

Figure 5:
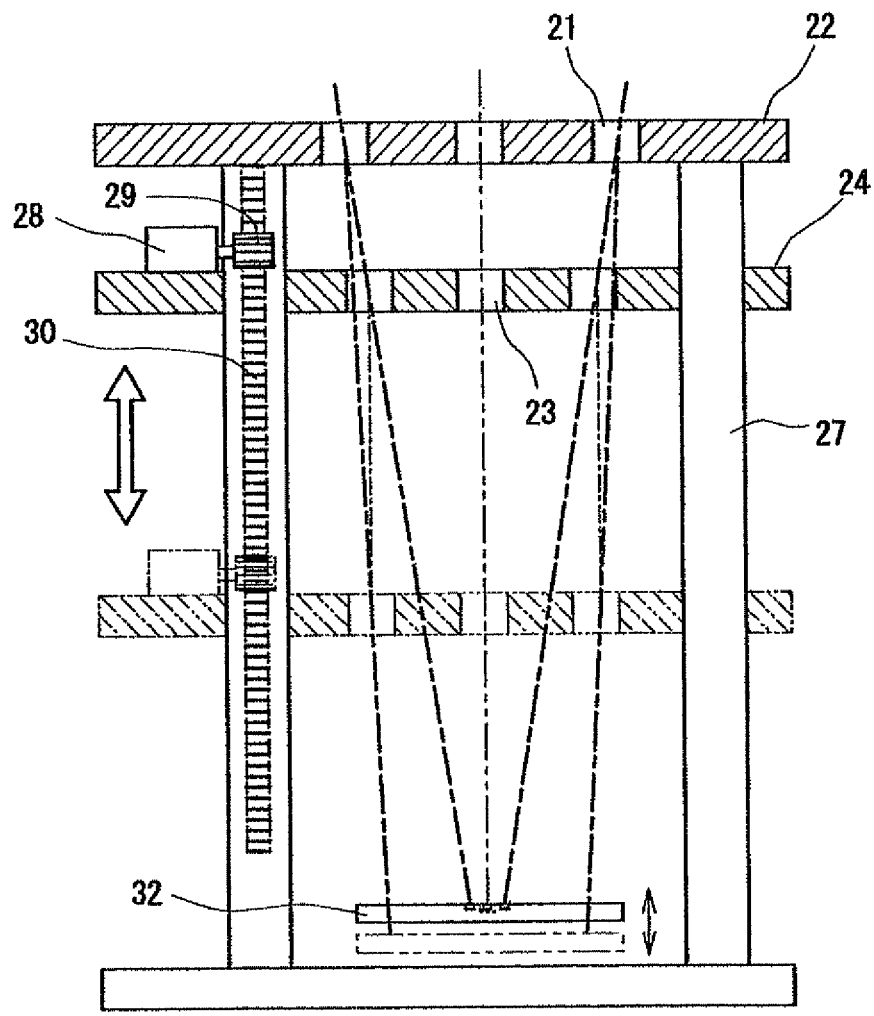
FIG. 5 is a diagram for describing a lower-plate varying mechanism according to the third embodiment.

To move the lower plate 24 up and down, for example, a motor 28 fixed to the lower plate 24 may drive to rotate a gear 29, which meshes with a rack gear 30 formed in the support column 27, as illustrated in FIG. 5. With this configuration, the lower plate 24 can be moved up and down to an arbitrarily-determined position. In addition, as FIGS. 4A and 4B illustrate, a microarray 32 is supported so as to be capable of moving in X, Y, and Z directions. Accordingly, while the height of the tips of the capillaries is changed in accordance with the position of the lower plate 24, the height of the microarray 32 is adjusted in accordance with the change in the height of the tips of the capillaries.

Figure 6A:
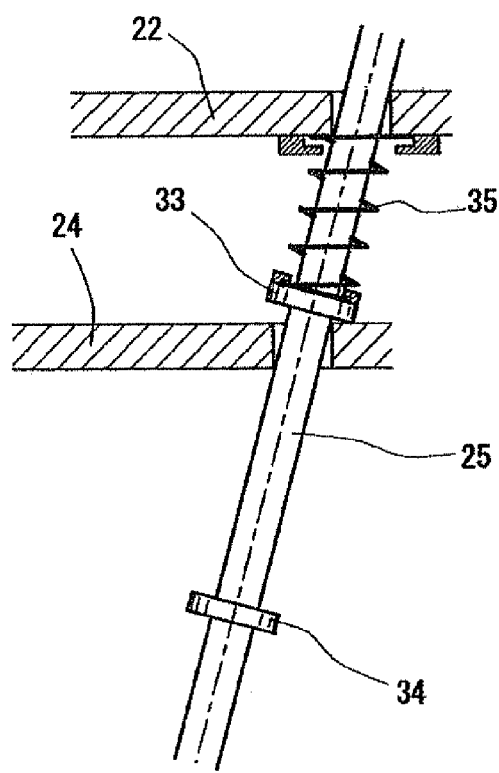
FIGS. 6A and 6B are diagrams illustrating a form of the third embodiment using stoppers.
Figure 6B:
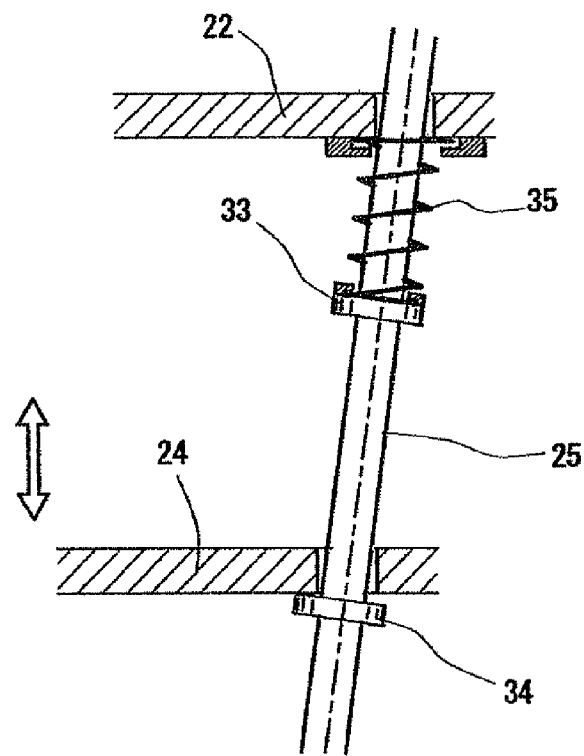

As an alternative form, an upper stopper 33 and a lower stopper 34 may be fixed to each capillary 25, and to hold the capillary 25, a spring 35 may be provided with its upper-end portion fixed to a fixing tool provided on the bottom surface of the upper plate 22 while the lower-end portion of the spring 35 is fixed to a fixing tool of the upper stopper 33, as FIGS. 6A and 6B illustrate. The lower plate 24 is thus allowed to move between the upper stopper 33 and the lower stopper 34. Suppose a case, for example, where the lower plate 24 is pushed down from a position the lower plate 24 is in contact with the upper stopper 33 as illustrated in FIG. 6A to a lower position as illustrated in FIG. 6B. In this case, when the capillary 25 is about to be pushed down by a frictional force, the spring 35 exerts a force to push the capillary 25 back to a predetermined position. Accordingly, the bottom-end portions of the multiple capillaries 25 are prevented from being randomly positioned, and thus are kept on forming a flat plane.

Fourth Embodiment

Figure 7A:
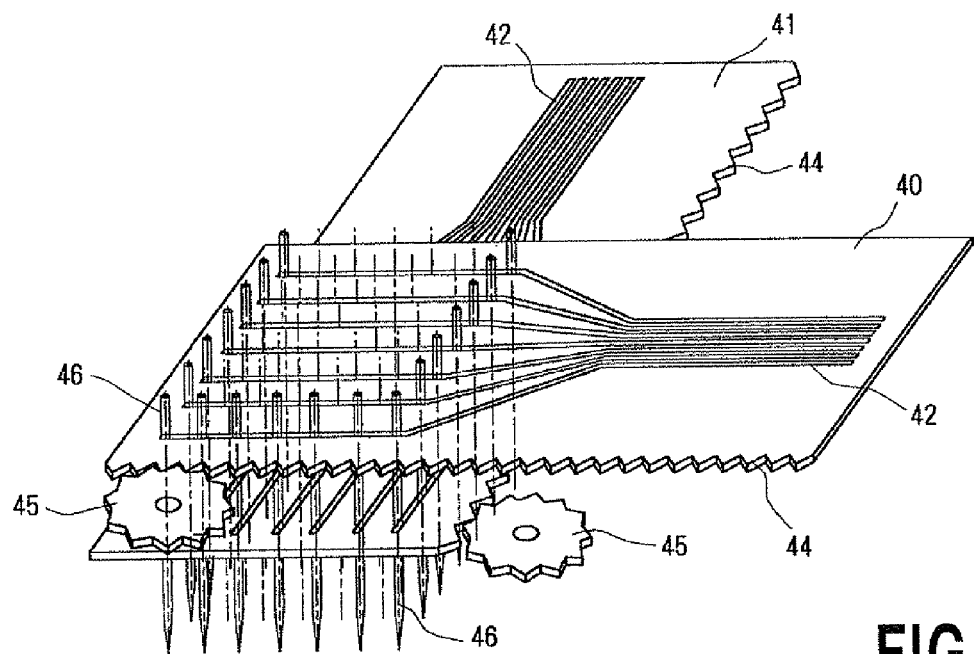
FIGS. 7A and 7B are schematic perspective views illustrating an example of a spotting-head-pitch varying apparatus with an upper flat plate and a lower flat plate having lengthwise open grooves and a crosswise open grooves, respectively, pitches between the adjacent grooves varying, according to a fourth embodiment of the present invention.
Figure 7B:
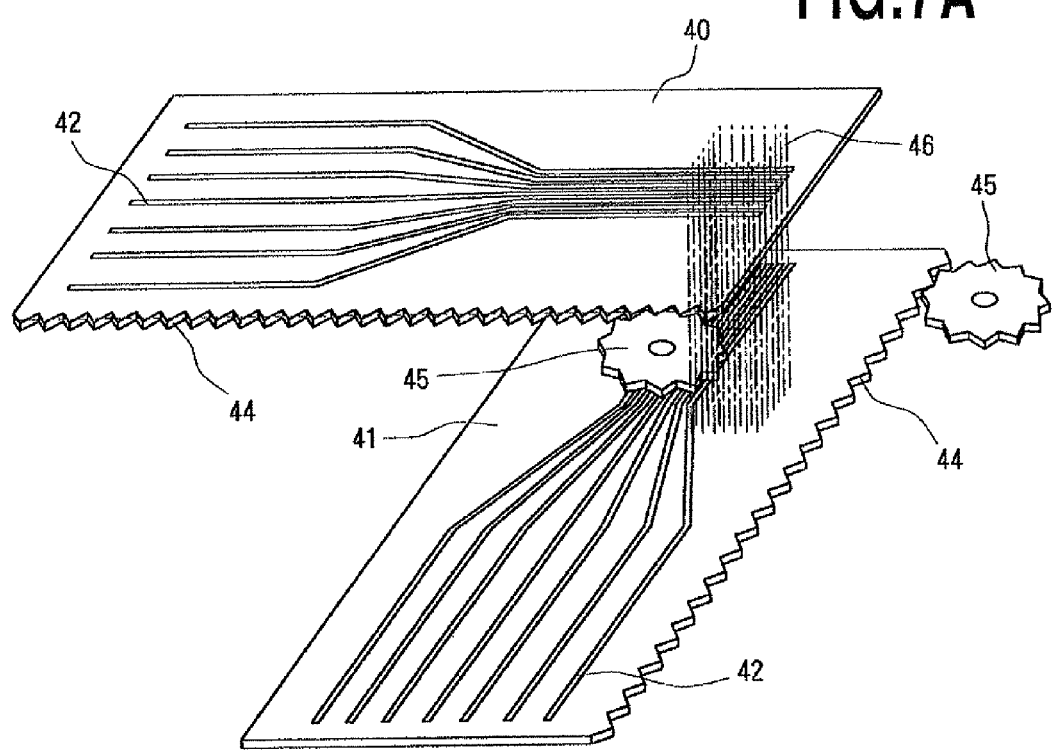

A mechanism employed in the embodiment illustrated in FIGS. 7A and 7B has the following configuration. Lines of open grooves 42 are formed in an upper plate 40 and in a lower plate 41. The open grooves 42 of each plate are arranged with a pitch corresponding to the state before spotting at a first-end side and with another pitch corresponding to the state after spotting at the second-end side. The plate 40 and the plate 41 intersect at right angles when viewed in the vertical direction. The grooves 42 of the plates 40 and 41 thus placed form holes arranged in a lattice shape, and capillaries 46 are supported respectively in the holes thus formed. As illustrated in FIGS. 7A and 7B, the size of the lattice is expanded or diminished by the reciprocating movement of the upper plate 40 and that of the lower plate 41, so that the distance between adjacent capillaries widens or narrows. To allow smooth movement of the capillaries 46 between their respective positions with the pre-spotting pitch corresponding to the state before spotting and their respective positions with the post-spotting pitch, the open grooves 42 are formed, when appropriate, to have oblique or curved sections along the way.

Figure 8A:
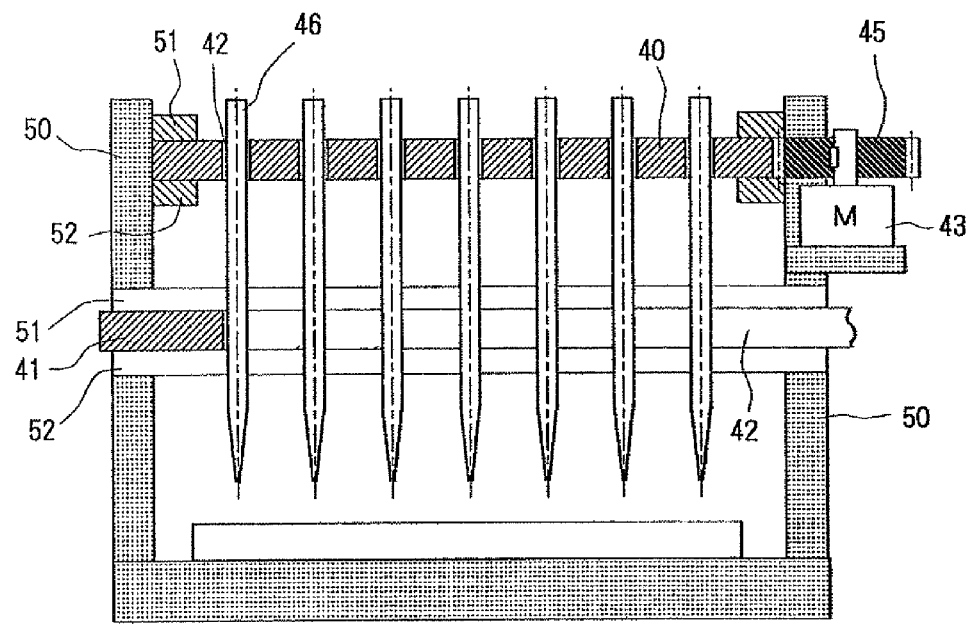
FIGS. 8A and 8B are sectional views illustrating the fourth embodiment together with frames.
Figure 8B:
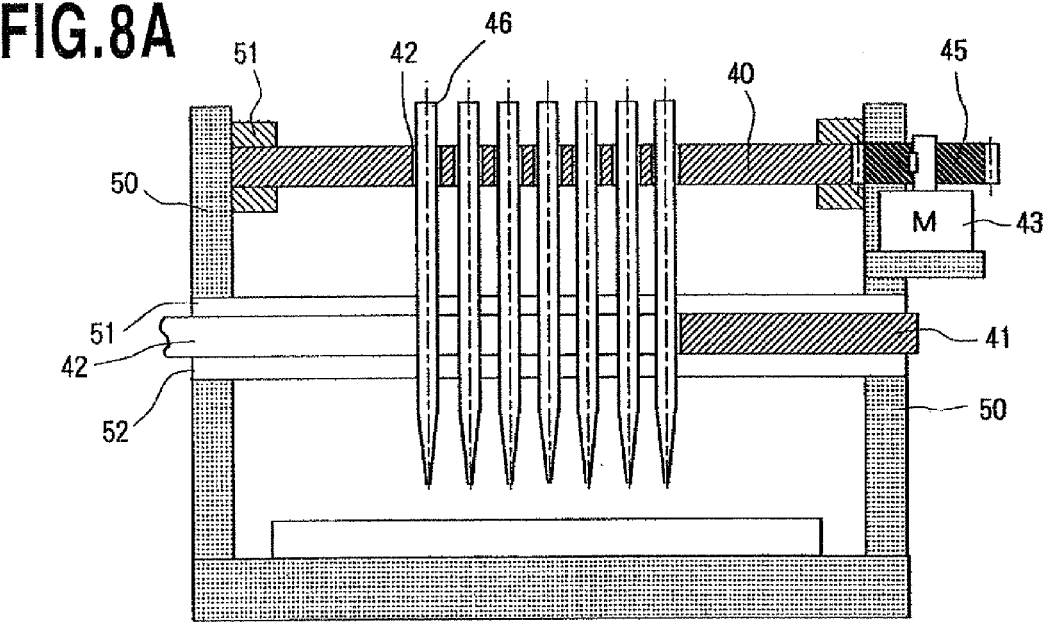
Figure 9A:
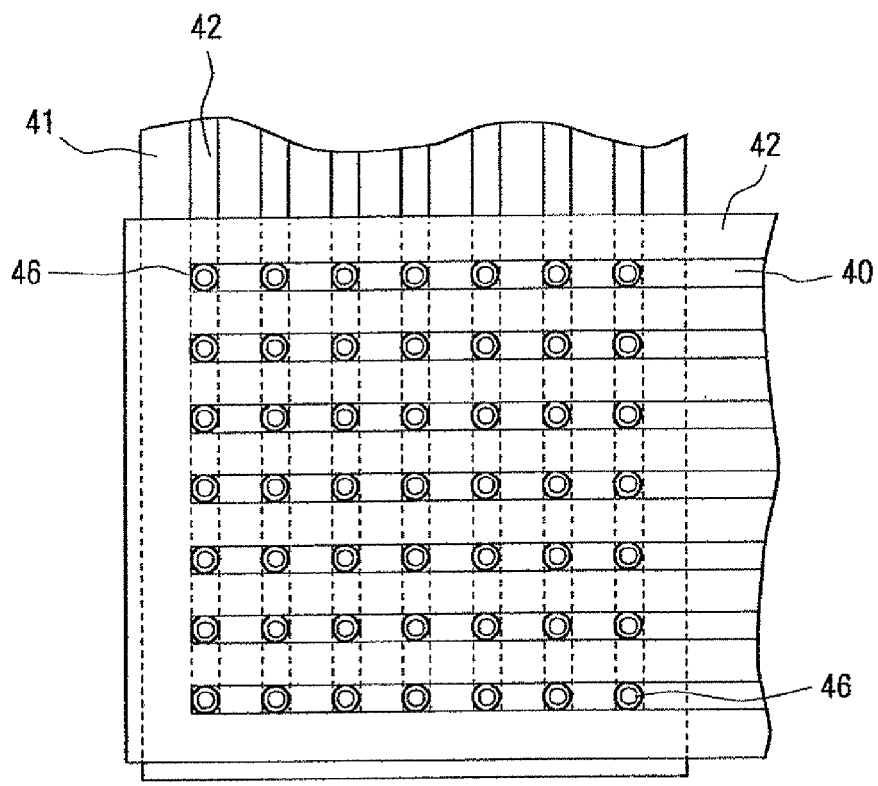
FIGS. 9A and 9B are top plan views illustrating how the pitch is changed according to the fourth embodiment.
Figure 9B:
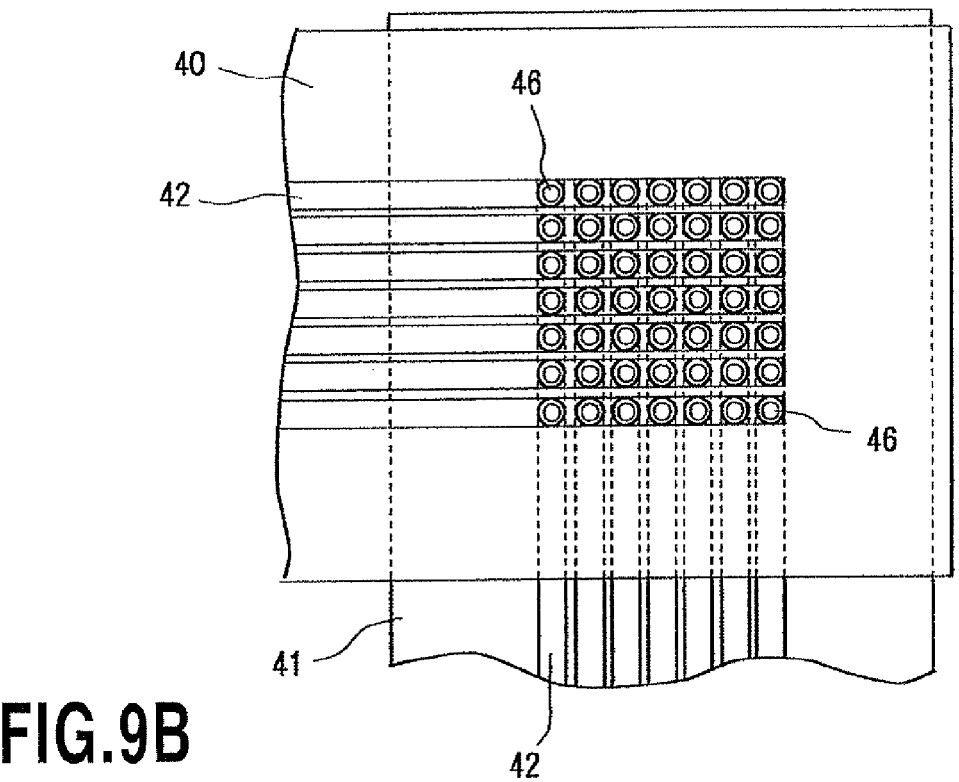

In the example illustrated in FIGS. 7A and 7B, a rack gear 44 is provided in a side portion of each of the top plate 40 and the bottom plate 41 along the moving direction of the same plate. Pinion gears 45 that are provided in frames or the like of the body mesh respectively with the rack gears 44. Motors M are provided to drive each of the pinion gears 45 for the upper plate 40 and for the lower plate 41 so as to make the two pinion gears 45 work in a coordinated fashion. In this event, for example, as FIGS. 8A and 8B illustrate, the upper plate 40 is allowed to move sliding between upper-plate guides 51 and 52 that are disposed with an in-between space in upper portions of frames 50 located respectively at the two end portions of the upper plate 40. The pinion gear 45 designed to be driven by a motor 43 fixed to the frame 50 meshes with the rack gear 44 of the upper plate 40. Likewise, the lower plate 41 designed to move sliding in a direction that is perpendicular to the moving direction of the upper plate 40 is placed between lower-plate guides 51 and 52, which are disposed with an in-between space in lower portions of frames. As in the case of the upper plate 40, the lower plate 41 is driven by an unillustrated motor that is provided in the frame. With this configuration, as FIGS. 8A and 8B illustrate, the capillaries 46 can be arranged with the pre-spotting pitch or with the post-spotting pitch. FIGS. 9A and 9B illustrate the lattice expanded and diminished states having the pre-spotting pitch and with the post-spotting pitch, respectively.

Figure 10A:
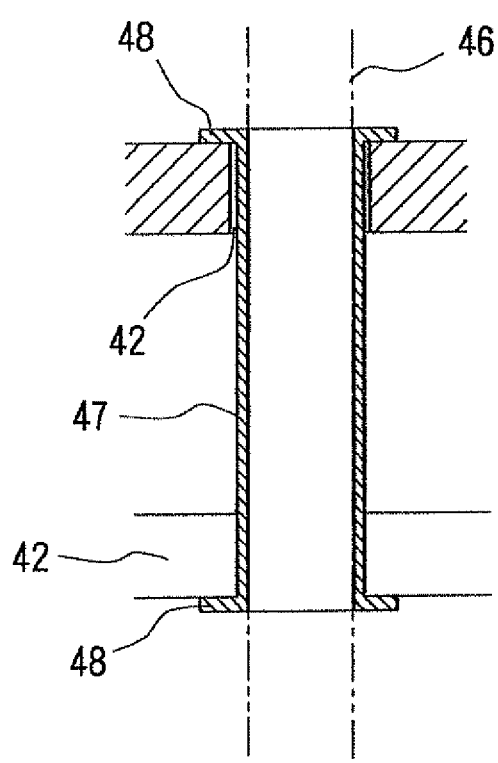
FIGS. 10A and 10B are views illustrating an example of a guide pipe used in the fourth embodiment.
Figure 10B:
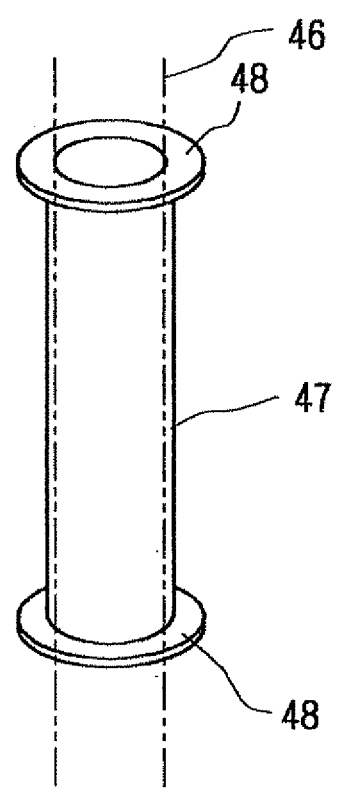

During the expanding and diminishing action of the lattice as described above, the capillaries have to be prevented from twisting. To this end, as FIGS. 10A and 10B illustrate, guide pipes 47 may be provided so as to penetrate both the upper plate 40 and the lower plate 41 and to be free to move sliding. Each guide pipe 47 is strong enough and has a large enough diameter to hold the corresponding capillary 46. Flanges 48 may be provided in the guide pipes so as to render the action more stable.

Fifth Embodiment

Figure 12A:
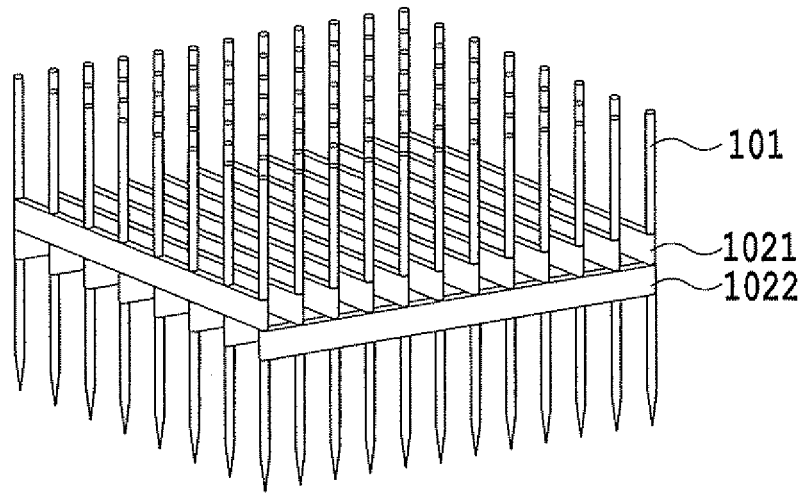
FIGS. 12A and 12B are views schematically showing a configuration of a pitch varying mechanism used in the fifth embodiment, which illustrate in the state that an array pitch between the capillaries is expanded to a maximum size.
Figure 12B:
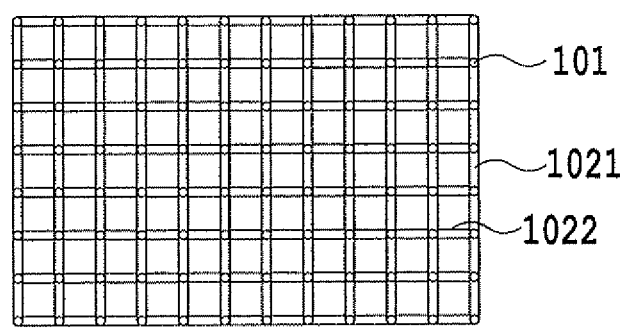
Figure 13A:
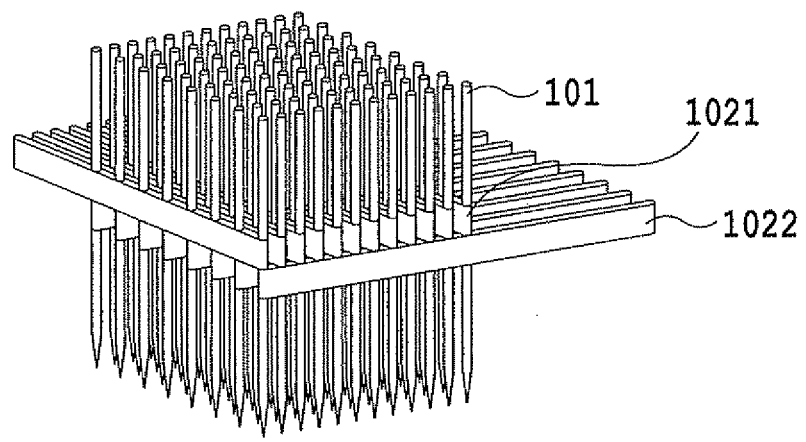
FIGS. 13A and 13B are views showing the state that the array pitch between the capillaries in the pitch varying mechanism in FIGS. 12A and 12B is set to a medium size.
Figure 13B:
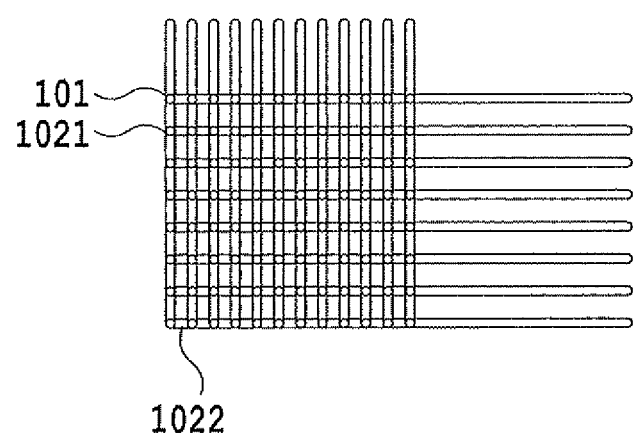
Figure 14A:
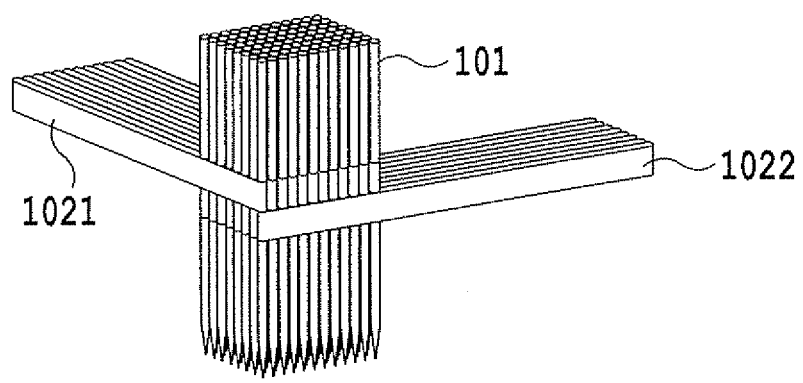
FIGS. 14A and 14B are views showing the state that the array pitch between the capillaries in the pitch varying mechanism in FIGS. 12A and 12B is set to a minimum size.
Figure 14B:
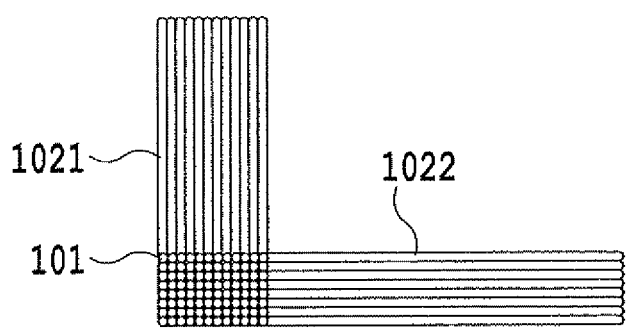

FIGS. 12A to 14B schematically illustrate a pitch varying mechanism used in a spotter according to the fifth embodiment of the present invention. FIGS. 12A, 13A and 14A are perspective views. FIGS. 12B, 13B and 14B are top views. In the embodiment shown in FIGS. 12A to 14B, the pitch varying mechanism has a plurality of lengthwise guiding members 1021 arranged in a lengthwise direction and a plurality of crosswise guiding members 1022 arranged in a crosswise direction.

Each of the lengthwise guiding members 1021 has a guiding hole for guiding plural capillaries 101 inserted therein in the lengthwise direction. Each of the crosswise guiding members 1022 is arranged orthogonally to the lengthwise guiding member 1021 and has a guiding hole for guiding plural capillaries 101 inserted therein in the crosswise direction. In addition, each of the lengthwise guiding members 1021 movably guides a distal portion of the capillary 101 in up and down directions in cooperation with each of the crosswise members 1022.

As shown in FIGS. 12A to 14B, an array pitch of the capillaries 101 in the crosswise direction can be varied by changing intervals between the lengthwise guiding members 1021 and an array pitch of the capillaries 101 in the lengthwise direction can be varied by changing intervals between the crosswise guiding members 1022.

Figure 15A:
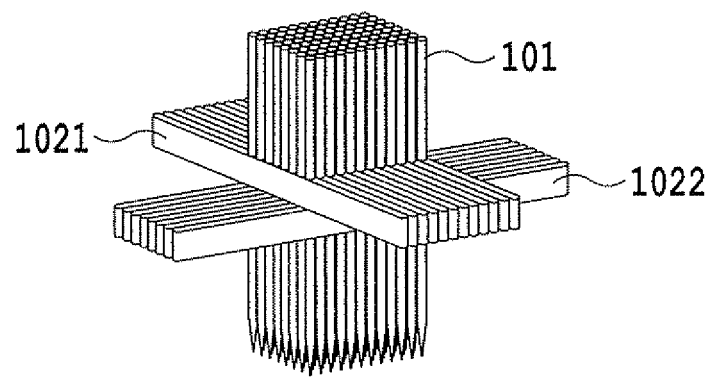
FIGS. 15A and 15B is a view illustrating the state that the entire capillaries in the pitch varying mechanism in FIGS. 12A and 12B is moved from the position in FIGS. 14A and 14B to another position.
Figure 15B:
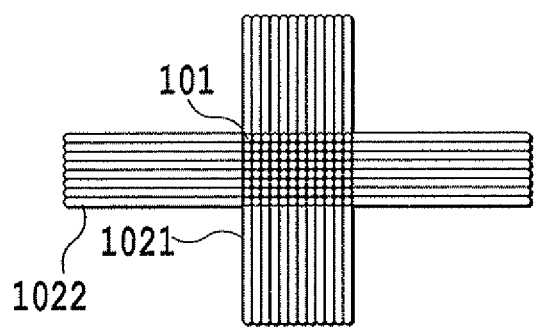

As shown in FIGS. 15A and 15B, the entire plural capillaries 101 can be moved by relative movement between the lengthwise guiding members 1021 and the crosswise guiding members 1022.

Figure 16:
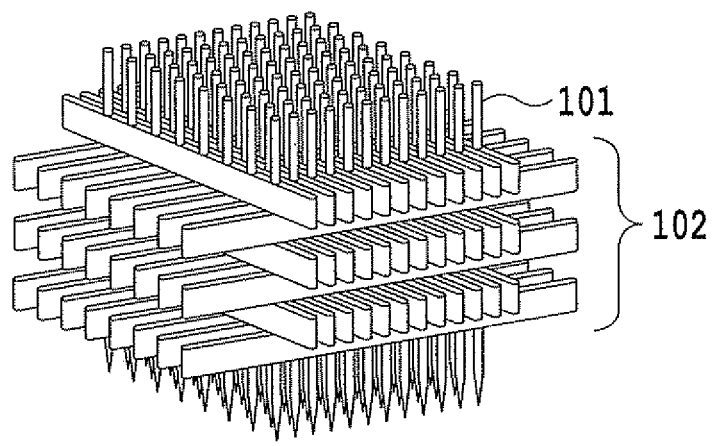
FIG. 16 is a view showing a variation of the pitch varying mechanism in FIGS. 12A and 12B.

Alternatively, as shown in FIG. 16, some set of lengthwise guiding members 1021 and the crosswise guiding members 1022 can be stacked to credibly keep the distal portion of each of the flexible capillaries 101 in a straight line.

Figure 17A:
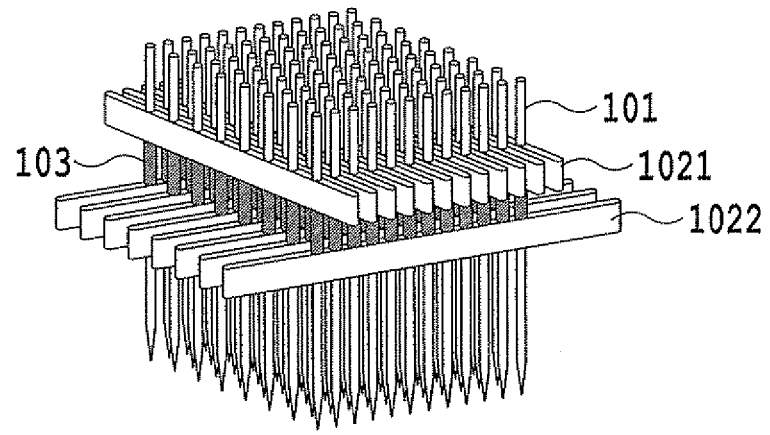
FIGS. 17A to 17C are other variations of the pitch varying mechanism in FIGS. 12A and 12B.

As described above, the capillaries 101 are movable in the up and down directions, respectively. Accordingly, a distal end position of each of the capillaries 101 can be defined by attaching a stopper 103 to each thereof, as shown in FIG. 17A. In FIG. 17A, each of stoppers 3 is in a contact with the lengthwise guiding member 1021 or the crosswise guiding member 1022, so that movement thereof in up and down directions can be restrained. As a result, the distal end of the capillary 101 can be positioned to a predetermined position.

Figure 17B:
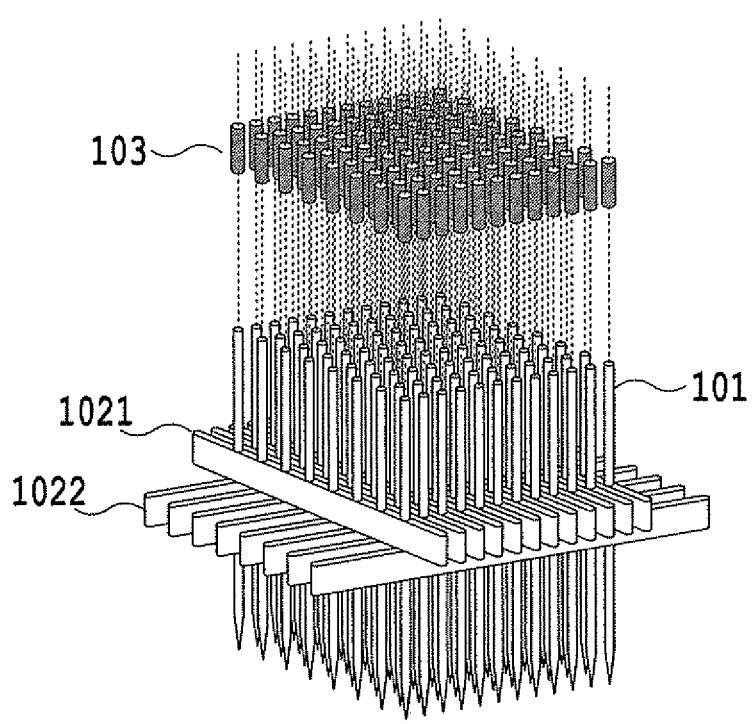
Figure 17C:
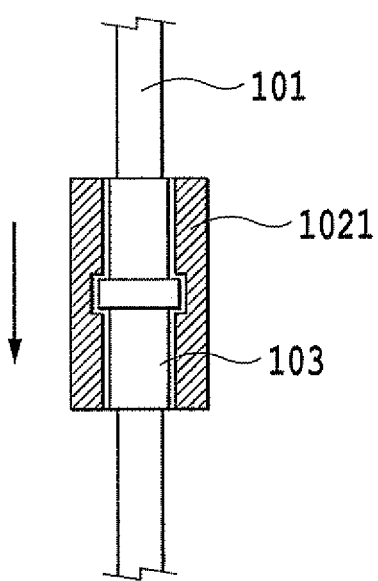
Figure 19:
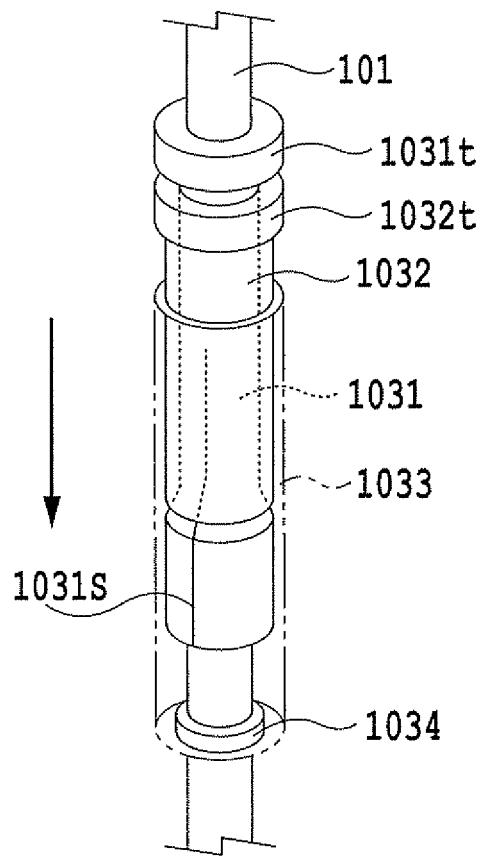
FIG. 19 is a perspective view of the clamping mechanism in FIGS. 12A and 12B.

A position of the stopper 103 to be attached does not limited to between the lengthwise guiding member 1021 and the crosswise guiding member 1022. For example, as shown in FIG. 17B, it is possible to locate the stopper 103 at a predetermined position away from the lengthwise guiding member 1021 and constrain the movement of the stopper 103 at the predetermined position. Further, as shown in FIG. 17C, it is also possible to engage the stopper 103 with the lengthwise guiding member 21 or the crosswise guiding member 1022 so that the stopper 103 can move in a longitudinal direction of the member 1021 or 1022.

Figure 21:
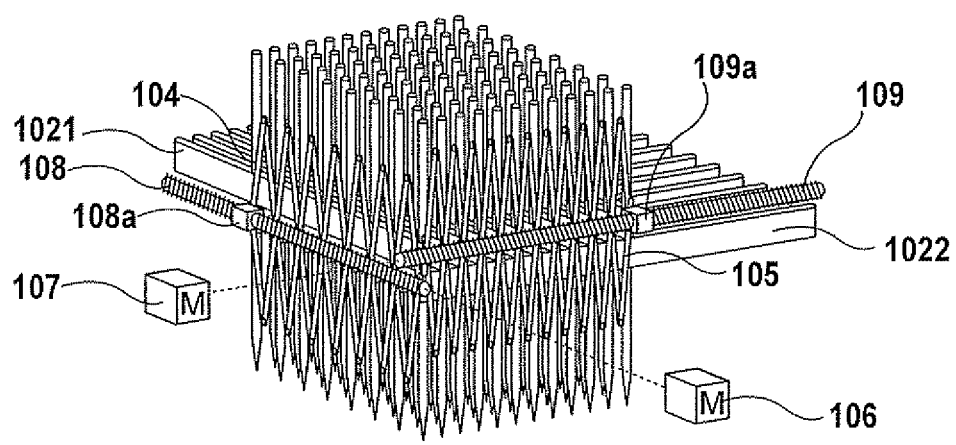
FIG. 21 is a perspective view showing an example of driving mechanism for the pitch varying mechanism in FIGS. 12A and 12B.

FIG. 21 is a perspective view showing an example of a stopper mechanism with a clamping mechanism. The stopper mechanism 103 has a clamping member 1031 into which the capillary 1 is inserted, a locking member 1032 into which the clamping member 1031 is inserted, a cylindrical member 1033 into which the clamping member 1032 is inserted, and an O-ring 1034 fitted with the capillary 101. The clamping member 1031 with a cylindrical shape has an annular protrusion 1031t at the top end, and a plurality of slits 1031s on the bottom side. The clamping member 1031A has clamping portions defined by the slits 1031s which are elastically deformable and expand outward in an unclamped state. The locking member 1032 with a cylindrical shape has an annular protrusion 1032t at the top end and a bottom end which is engageable with the clamping portions of the clamping member 1031A to lock the clamping portions.

An operation of the above clamping mechanism will be described below with reference to FIG. 18A to FIG. 18D. In the state shown in FIG. 18A, the stopper mechanism 3 clamps the capillary 101. The clamping portions of the clamping member 1031 are contracted by the engagement with the locking member 1032 so that the capillary 1 is clamped thereby. The top end of the clamping member 1031 is connected to the guiding member 1021.

The guiding member 1021 is moved downwards from the position shown in FIG. 18A so as to push down the clamping member 1031 and the locking member 1032, so that the capillary 1 is slid relative to the O-ring 1034 and is moved forward by the movement amount of the clamping member 1031, as shown in FIG. 18B. In addition, the locking member 1032 is moved to a position where the protrusion 1032t contacts with the top end of the cylindrical member 1033.

The guiding member 1021 is moved further downwards from the position shown in FIG. 18B so as to move down the guiding member 1021 relative to the clamping member 1031, as shown in FIG. 18C, so that the engagement of the locking member 1032 with the clamping member 1031 is released. As a result, the clamping portions of the clamping member 1031 are expanded and the capillary 101 is unlocked.

As shown in FIG. 18D, the guiding member 1021 is returned to the original position so as to move up the clamping member 1031, so that the clamping member 1031 engages with locking member 1032 again. The clamping portions are contracted inward against elastic force and the capillary 101 is clamped again.

Figure 20:
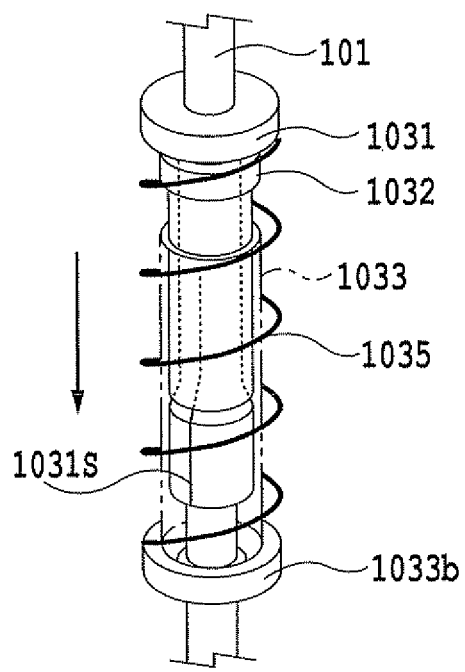
FIG. 20 is a perspective view of a variation of the clamping mechanism in FIGS. 12A and 12B.

In the case that the clamping member 1031 is not connected to the guiding member 1021, as shown in FIG. 20, a spring 1035 is arranged between the clamping member 1031 and the bottom end portion 1033b of the cylindrical member 1033. The spring 1035 can return the clamping mechanism from the unclamped state to the clamped state.

Alternatively, it is possible to adjust the distal end position of the capillary 101 by putting the distal end of the capillary 101 in the unclamped state toward a datum surface. Further, the capillary 101 in the unclamped state can be moved forward by a motor and the like. An actuator using shape memory alloy instead of the motor also can be employed.

FIG. 21 is a perspective view schematically showing an example of driving mechanism for driving the pitch varying mechanism. In FIG. 21, a plurality of pantograph mechanisms 104 link between the plurality of the guiding members 1021 and a plurality of pantograph mechanisms 105 link between the plurality of the guiding members 1022, respectively. Pantograph mechanisms 104 and 105 located on one end of the pitch varying mechanism are fixed to predetermined positions, respectively. Pantograph mechanisms 104 and 105 located on the other end of the pitch varying mechanism are connected to movable members 108a and 109a, respectively. Screw shafts 108 and 109 are screwed into the movable members 108a and 109a, respectively. The array pitches of the capillaries 101 in the lengthwise and crosswise directions can be varied by driving motors connected to the screw shafts 108 and 109, respectively.

Note that, in each of the above-described embodiments, the plural spotting heads form an m×n array (m, n≥1) with m spotting heads arranged lengthwise and n spotting heads crosswise. Accordingly, a case where either m or n is 1 is included in the above-described embodiments. To put it differently, the present invention can be carried out even when the spotting heads are arranged in a single line either lengthwise or crosswise.

Besides the above-described embodiments, the present invention can be carried out in various forms. In the forms described in the above-described embodiment, the pitch of the spotting heads is changed equidistantly between the state when the sample solutions are collected and the state when the sample solutions are spotted. Such forms are described simply as an exemplar forms in which the present invention is commonly carried out. Suppose, as an alternative embodiment, a case where the pitch between the array at the collection and the array at the spotting is not transformed but where the entire array shape of the array spots is turned. In this case, such turning of the array shape can be accomplished by turning the apparatus that supports the plural spotting heads or by turning the stage on which the substrate is mounted. This transformation in the array shape of the array spots by turning can be employed even when the pitch of the spotting heads is transformed between the collection and the spotting.

In addition, for example, in the embodiment illustrated in FIGS. 3A to 3F, both the first shaft 11 and the second shaft 12 that are orthogonal to one another is stretched or contracted so as to have the identical pitch. In an alternative embodiment, the pitch of the shafts 1 and the pitch of the shafts 12 may differ from each other, so that even the square array shape seen from above at the collection can be transformed into a predetermined rectangular array shape at the spotting. Note that, also in this case, the array shape can be turned between the collection and the spotting as in the above-described case.

Moreover, in the embodiment illustrated in FIGS. 7A to 10B, the transformation in the array shape takes place between the array shape at the collection and the similarly-diminished array shape thereof at the spotting. When the distance between adjacent open grooves 42 of the array in the upper plate 40 differs from the distance between adjacent open grooves 42 of the array in the lower plate 41 both at the collection and at the spotting, the mechanism can deal with an arbitrarily-determined rectangular shape with an arbitrarily-determined distance between adjacent spotting heads. In addition, the embodiment illustrated in FIGS. 7A to 10B describes a case where the array at the collection and the array at the spotting are linked to each other by means of the obliquely-formed grooves arranged with gradually-changing distance left in between, and the transformation between the arrays are guided by such grooves. When the oblique grooves are formed to be sufficiently long, the array shape at the spotting can be an arbitrarily-determined quadrilateral by performing the spotting at a position in the oblique grooves. In this way or another, the present invention can be carried out in still different forms.

Figure 11A:
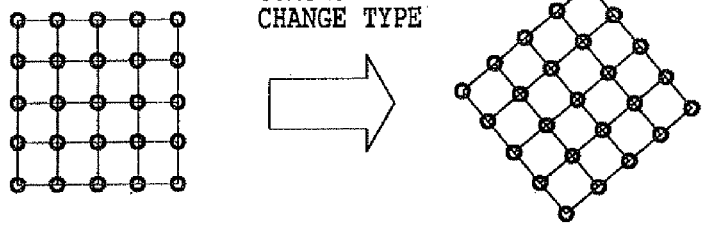
FIGS. 11A to 11D are diagrams for describing various types of changes in array shape of array spots.
Figure 11B:
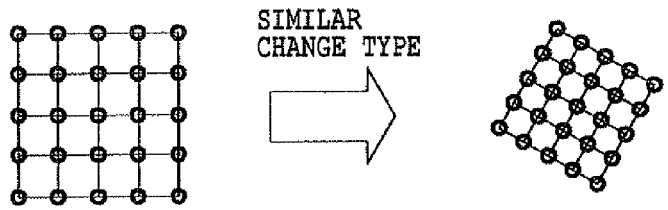
Figure 11C:
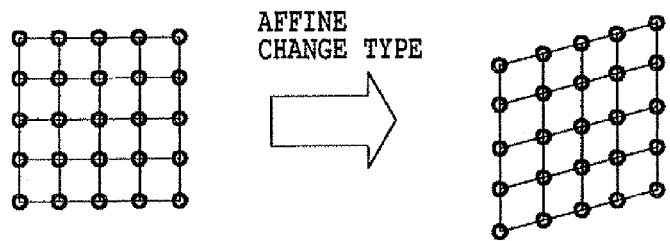
Figure 11D:
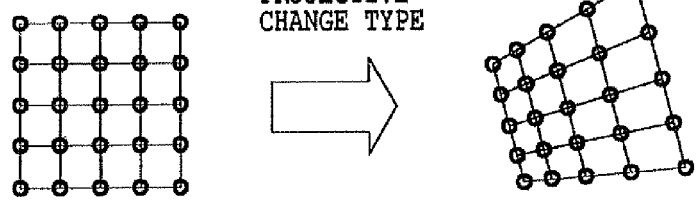

As described above, the present invention can be carried out in various forms, which are illustrated, in a summarized fashion, in FIGS. 11A to 11D. FIGS. 11A to 11D summarizes various forms of the changing in the array shape of the array spots formed by the placement positions of the spotting heads from the first position (at the collection) to the second position (at the spotting). FIG. 11A illustrates a case where the array shape at the first position (1) is congruent with the array shape at the second position (2), and only the turning is carried out. FIG. 11B illustrates a case where the array shape is transformed to a similar shape and the turning is carried out when necessary. FIG. 11C illustrates a case where the array shape at the first position (1) is transformed to various shapes, such as the illustrated one, at the second position (2) by an affine change. FIG. 11D illustrates a case where the array shape at the first position (1) is transformed to various shapes, such as the illustrated one, at the second position (2) by a projective change. In addition, when necessary, a phase-change-type change—a flat-plane array changed to a curved-surface array as FIG. 11E illustrates—can be conceived of as another form. Also conceivable is an exchange-transformation-type change in which the placement points for the spotting heads are exchanged arbitrarily. The present invention can be carried out in these arbitrarily forms when necessary.

Included in the various types of transformation in the array shape, such as the ones described above, are: a transformation accomplished by moving the array only in a first one of the three axial directions (in X-axis direction) by means of a driving apparatus, and by letting the array be moved in the other two directions in conjunction with the movement in the first one of the three axial directions, so that the entire shape is transformed; a transformation accomplished by moving in the two directions (in X-axis direction and in Y-axis direction) by means of their respective driving means; a transformation accomplished by the movement in all of the three axial directions (X-axis, Y-axis, and Z-axis). Also in the present invention, such various types of transformations can be applied to various embodiments or to various forms described above.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined by appended claims.

What is claimed is:

1. A spotter comprising:
   a plurality of spotting heads, each of the plurality of spotting heads having a discharging portion at a tip portion, the plurality of spotting heads form an m×n array (m, n>1) with m spotting heads arranged lengthwise and n spotting heads arranged crosswise; and
   a pitch varying mechanism configured to continuously vary an array pitch of the plurality of spotting heads arrayed in a lengthwise direction and an array pitch of the plurality of spotting heads arrayed in a crosswise direction,
   the pitch varying mechanism comprising:
      a first movable member being supported movably with respect to the plurality of spotting heads arrayed in the crosswise direction, the first movable member having m first open grooves, the n spotting heads arrayed in the crosswise direction being inserted into each of the m first open grooves, respectively, and
      a second movable member being supported movably with respect to the plurality of spotting heads arrayed in the lengthwise direction, the second movable member having n second open grooves, the m spotting heads arrayed in the lengthwise direction being inserted into each of the n second open grooves, respectively,
   each of the m first open grooves comprising:
      a first pitch portion setting the array pitch of the plurality of spotting heads arrayed in the lengthwise direction to a first pitch,
      a second pitch portion setting the array pitch of the plurality of spotting heads arrayed in the lengthwise direction to a second pitch, the second pitch being different from the first pitch, and
      a connecting portion connecting between the first pitch portion and the second pitch portion,
   each of the n second open grooves comprising:
      a third pitch portion setting the array pitch of the plurality of spotting heads arrayed in the crosswise direction to a third pitch,
      a fourth pitch portion setting the array pitch of the plurality of spotting heads arrayed in the crosswise direction to a fourth pitch, the fourth pitch being different from the third pitch, and
      a connecting portion connecting between the third pitch portion and the fourth pitch portion,
   wherein the array pitch of the plurality of spotting heads arrayed in the lengthwise direction is varied between the first pitch and the second pitch by a reciprocation of the first movable member, and the array pitch of the plurality of spotting heads arrayed in the crosswise direction is varied between the third pitch and the fourth pitch by a reciprocation of the second movable member,
   wherein each of the plurality of spotting heads extends through both the first movable member and the second movable member, and
   wherein the array pitch in the lengthwise direction or the array pitch in the crosswise direction is adjustable to a desirable pitch between the first and second pitches or between the third and fourth pitches.

2. The spotter according to claim 1, wherein the pitch varying mechanism adjusts the array pitch of the plurality of spotting heads so as to be identical to an array pitch of a plurality of sample containers arranged at an equal pitch, and so as to be identical to an array of positions where sample solutions are to be spotted.

3. The spotter according to claim 2, wherein the pitch varying mechanism makes the plurality of spotting heads carry out simultaneous spotting of a plurality of sample solutions in an array.

4. The spotter according to claim 3, wherein the pitch varying mechanism includes a mechanism that:
   allows the plurality of spotting heads to keep distances between adjacent spotting heads equal to one another when the pitch is wide,
   allows adjacent spotting heads to be in contact with one another when the pitch is narrow, and
   is capable of maintaining the discharging portions of the plurality of spotting heads on a single plane both when the pitch is wide and when the pitch is narrow.

5. The spotter according to claim 1, wherein the entire spotting head including the discharging portion is formed of a capillary that is flexible.

6. A spotter comprising:
   a plurality of spotting heads, each of the plurality of spotting heads having a discharging portion at a tip portion, the plurality of spotting heads form an m×n array (m, n>1) with m spotting heads arranged lengthwise and n spotting heads arranged crosswise; and
   a pitch varying mechanism configured to continuously vary an array pitch of the plurality of spotting heads in a lengthwise direction and an array pitch of the plurality of spotting heads in a crosswise direction,
   the pitch varying mechanism comprising:
      a first plate having holes formed in an array corresponding to spotting positions,
      a second plate having holes formed in an array that is similar to the array corresponding to the spotting positions,
      the first plate and the second plate being disposed to each other with a distance therebetween and holding the plurality of spotting heads, each spotting head of the plurality of spotting heads penetrating a hole of the first plate and a hole of the second plate, the two holes being located at a position of similarity, and
      a support column extending in a direction perpendicular to the first and second plates and of which opposite ends are fixed, the support column being inserted into the first and second plates so as to movably guide one of the first and second plates in the direction perpendicular to the first and second plates,
   wherein the pitch of the plurality of spotting heads is varied larger or smaller when the distance between the first plate and the second plate is widened or narrowed, and
   wherein the pitch of the plurality of spotting heads is adjustable to a desirable pitch between a maximum pitch and a minimum pitch.

7. The spotter according to claim 6, wherein the entire spotting head including the discharging portion is formed of a capillary that is flexible.

* * * * *

UNITED STATES PATENT AND TRADEMARK OFFICE
CERTIFICATE OF CORRECTION

PATENT NO. : 8,663,577 B2
APPLICATION NO. : 12/385755
DATED : March 4, 2014
INVENTOR(S) : Hiroshi Aoki et al.

Page 1 of 1

It is certified that error appears in the above-identified patent and that said Letters Patent is hereby corrected as shown below:

In the Claims

Column 13 lines 16-20 should read:

1. A spotter comprising:
a plurality of spotting heads, each of the plurality of spot-
ting heads having a discharging portion at a tip portion,
the plurality of spotting heads form an m×n array (m,
n≥1) with m spotting heads arranged lengthwise and n Column 14 lines 31-35 should read:

6. A spotter comprising:
a plurality of spotting heads, each of the plurality of spot-
ting heads having a discharging portion at a tip portion,
the plurality of spotting heads form an m×n array (m,
n≥1) with m spotting heads arranged lengthwise and n Signed and Sealed this
Fifth Day of May, 2015

Michelle K. Lee
*Director of the United States Patent and Trademark Office*